United States Patent
Gracey

(10) Patent No.: US 6,620,975 B2
(45) Date of Patent: Sep. 16, 2003

(54) PROCESS FOR MAKING BUTYL ETHERS OF GLYCOLS

(75) Inventor: Benjamin Patrick Gracey, Hull (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/844,442

(22) Filed: Apr. 30, 2001

(65) Prior Publication Data

US 2002/0065438 A1 May 30, 2002

Related U.S. Application Data

(63) Continuation of application No. PCT/GB99/03494, filed on Oct. 21, 1999.

(30) Foreign Application Priority Data

Nov. 2, 1998 (GB) ................................................ 9823980

(51) Int. Cl.[7] .......................... C07C 43/11; C07C 41/09
(52) U.S. Cl. ........................ 568/619; 568/678; 568/679
(58) Field of Search ................................ 568/619, 678, 568/679

(56) References Cited

U.S. PATENT DOCUMENTS

| 4,450,289 A | 5/1984 | Paxson | 560/241 |
| 4,843,180 A | 6/1989 | Mullins | 568/689 |
| 5,705,707 A | 1/1998 | Kanand et al. | 568/487 |

FOREIGN PATENT DOCUMENTS

| DE | 196 37 892 A1 | 3/1998 | C07C/43/14 |
| DE | 196 37 895 A1 | 3/1998 | C07C/43/04 |

*Primary Examiner*—Rosalynd Keys
(74) *Attorney, Agent, or Firm*—Nixon & Vanderhye

(57) ABSTRACT

Processes are described for the preparation of glycol butyl ethers involving reaction of butadiene with saturated aliphatic glycols, separating the thus formed n- and sec-butenyl glycol ethers and hydrogenating the n-butenyl glycol ethers. Additional features are the use in the first step of heterogeneous catalyst modified by alkylpyridinium quaternary ammonium, quaternary arsonium quaternary phosphonium counterions and/or the conversion of sec-butenyl glycol ethers to butadiene and saturated aliphatic glycols.

10 Claims, 2 Drawing Sheets

PROCESS FOR MAKING BUTYL ETHERS OF GLYCOLS

This is a continuation of PCT application No. PCT/GB9903494, filed Oct. 21, 1999, the entire content of which is hereby incorporated by reference in this application.

The present invention relates to a process for making butyl ethers of glycols by hydrogenation of the corresponding butenyl ethers. These can be made by reacting butadiene with a glycol in the presence of a Bronsted or a Lewis acid catalyst.

n-Butyl glycol ethers are valuable chemical commodities. Hitherto such glycol ethers have been produced by the reaction of n-butanol with an olefin oxide such as ethylene oxide. However, the selectivity of such a process is limited by the formation of a significant amounts of unwanted by-products such as diglycol- and triglycol ethers. The presence of these by-products adds complexity to the separation of the desired n-butyl mono glycol ethers. The loss of selectivity and the resultant complexity of separation can adversely affect the process economics.

It is also known that butadiene can be reacted with an alcohol to form a mixture of isomeric unsaturated ethers (e.g. DE2550902, U.S. Pat. No. 2,922,822, U.S. Pat. No. 4,843,180, EP0025240 and DE19637895).

U.S. Pat. No. 2,922,822, for example, discloses a method for making unsaturated ethers by reacting butadiene with an alcohol, in the presence of an active acid catalyst, e.g. a strongly acidic ion-exchange resin. The alcohol employed is preferably, a primary aliphatic monohydric alcohol. For example, when methanol is employed, the reaction produces two mono methyl ether isomers, which are separable by distillation. The patent recites that if one of these isomers is recycled to give an equilibrium mixture with the other and again separated, it is possible to produce predominantly one or the other isomer (col 2, lines 53 to 58).

More recently, U.S. Pat. No. 5,705,707 describes an application of this addition chemistry for making butyraldehyde and n-butanol. Butadiene is reacted with an alcohol in the presence of an acidic catalyst to form a mixture of isomeric unsaturated ethers. Thus the reaction of an alcohol with butadiene yields a mixture of isomeric adducts of formulae (a) and (b) as shown below:

$$CH_3.CH=CH.CH_2.OR \quad (a)$$

$$CH_2=CHCH(OR).CH_3 \quad (b)$$

Under acidic conditions, compound (b) (3-alkoxybut-1-ene, also known as sec-butenyl ether) is in equilibrium with compound (a) (1-alkoxybut-2-ene, also known as n-butenyl ether or crotyl ether). For the production of n-butyraldehyde (a) is further isomerised by a transition metal catalyst to a vinyl ether compound (c) of the formula:

$$CH_3-CH_2-CH=CH.OR \quad (c)$$

Compound (c) is then converted to the butyraldehyde in the liquid phase in the presence of a catalyst by hydrolysis. Hydrogenation of butyraldehyde results in the formation of butanol.

DE19637895(equivalent WO 98/12164) describes a process for preparing n-butyl alkyl ethers by I) reacting butadiene with a glycol to give a mixture of n-butenyl ether and secondary butenyl ether, II) separating the ether adducts produced, III) isomerising the secondary butenyl ether into the n-butenyl ether, and IV) hydrogenating the n-butenyl ether produced. The isomerisation step (III) maybe carried out in the same process stage as the initial reaction between the butadiene and the glycol (step I). Alternatively, the secondary butenyl ether adduct separated in step II may be isomerised in a separate isomerisation stage by contacting the adduct with an isomerisation catalyst. This reaction produces a mixture of the n-butenyl and secondary butenyl adducts. The n-butenyl adduct produced is isolated by fractional distillation and hydrogenated into the desired product.

We have now found that we can improve the productivity and selectivity of the butyl glycol ether production process by A) using a modified catalyst to catalyse the addition of butadiene to a saturated aliphatic glycol, and/or B) converting any unwanted ether adduct into the starting butadiene and glycol in a separate reaction zone.

Accordingly, a first aspect of the present invention provides a process for the production of a butyl glycol ether which comprises:

i. forming a mixture of n-butenyl glycol ether and secondary butenyl glycol ether by reacting butadiene with a saturated aliphatic glycol in the presence of a heterogeneous catalyst which is modified by the addition of at least one counterion selected from the group consisting of: an alkyl pyridinium, quaternary ammonium, quaternary arsonium and quaternary phosphonium;

ii. separating the n-butenyl ether and secondary butenyl glycol ether formed in step i), and iii. hydrogenating the n-butenyl ether separated in step ii) in the presence of a catalyst to the corresponding n-butyl ether.

Suitable counterions for the present invention are described in, for example, U.S. Pat. No. 4,450,287, U.S. Pat. No. 4,450,288 and U.S. Pat. No. 4,450,289. For instance, suitable pyridinium counterions have the formula $C_5H_5N_+R$, wherein R is a hydrocarbyl (e.g. an alkyl) having 1 to 30 carbon atoms, preferably more than 5 carbon atoms. Most preferably, the alkyl group is a straight chain alkyl group. One or more of the 5H's on the pyridinium ring may be substituted with an alkyl group, for example, a methyl or ethyl group.

Suitable quaternary ammonium counterions have the formula $NR_1R_2R_3R4$, where each of $R_1$, $R_2$, $R_3$ $R_4$ is a hydrocarbyl group having 1 to 30 carbon atoms. $R_1$, $R_2$, $R_3$ $R_4$ may be the same or different. Preferably the sum of the total number of carbon atoms is more than 15. Specific examples include:

$$N^+[(C_4H_9)]_4, N^+(CH_3)_3(C_{16}H_{33}), N^+(C_{12}H_{25})(CH_3)_3.$$

Suitable quaternary phosphonium counterions have the formula $PR_1R_2R_3R_4$, where each of $R_1$, $R_2$, $R_3$ $R_4$ is a hydrocarbyl group having 1 to 30 carbon atoms. Preferably, the sum of the number of carbon atoms in the phosphonium counterion is greater than 15. $R_1$, $R_2$, $R_3$ $R_4$ may be the same or different. Specific examples of such a quaternary phosphonium counterion include: $P^+(CH_3)_3(C_{16}H_{33})$, tetraphenyl phosphonium, and methyl triphenyl phosphonium ions.

Quaternary ammonium or quaternary phosphonium substituted ferrocene may also be employed as a counterion. Such counterions have the general formula:

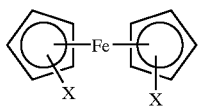

where X is a quaternary ammonium or quaternary phosphonium cation.

Specific examples of such counterions include:

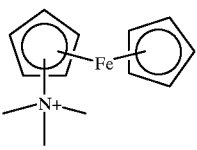

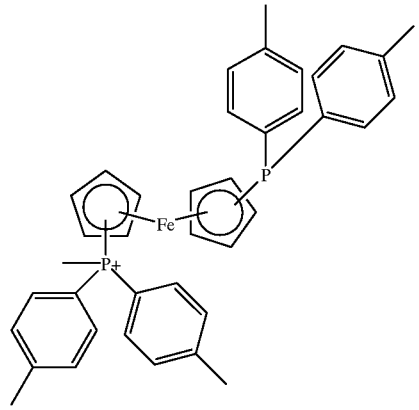

Such counterions are employed to modify heterogeneous catalysts. Suitable heterogeneous catalysts include sulphonic acid substituted polymers such as strong acid ion-exchange resins. Examples of such catalysts include sulphonic acid functionalised polymers of macrorecticular and gel type (e.g. ion exchange resins such as Amberlyst 15H®, Amberlyst IR120®, Amberjet 1500H®, Nafion®), phosphoric acid fuinctionalised polymers, supported heteropolyacids of tungsten or molybdenum and acidic oxides (such as HY zeolites). To modify these catalysts, the quaternary cations are ion exchanged. The starting salts may contain as counter anions halides, sulphates or carboxylates. The proportion of acid sites exchanged by these bulky counterions may be 1–40%, preferably 1–10%.

One advantage of using a heterogeneous catalysts is that it allows reaction products to be separated relatively easily from the reaction mixture. The heterogeneous catalyst phase can be liquid (e.g. liquid acidic polymers and partially solvated polymers) or a solid (e.g. HY zeolites, strong acid macrorecticular and gel type ion-exchange resins and heteropolyacids of tungsten or molybdenum which have been ion-exchanged and/or supported on a carrier material).

The secondary butenyl glycol ether (3-alkoxybut-1-ene) separated from the mixture of butenyl ethers may be recycled back to step i). This allows isomerisation to be suitably combined with the initial addition reaction stage.

In an alternative embodiment, the secondary butenyl glycol ether separated from the mixture of butenyl ethers may be catalytically isomerised to the n-butenyl glycol ether in a separate reaction step. An acid catalyst may be employed to catalyse this isomerisation. Suitable catalysts include Bronsted acids which are non-oxidising; complexes of Group Ib, VIIb or VIIIb of the Periodic Table such as e.g. the phosphine complexes of palladium or nickel; acidic zeolites such as zeolite-β, or zeolite Y; and ion-exchange resins of the Amberlyst® or Nafion® type. The isomerisation may suitably be carried out in the heterogeneous phase. Preferably, the isomerisation step is carried out under similar conditions to the first addition reaction stage (step i). Thus, in this preferred embodiment, the catalyst employed for isomerisation is modified by exchange with counterions.

The conditions employed for the conversion of sec-butenyl glycol ether into n-butenyl glycol ether may be suitable for an acid catalysed liquid phase reaction.

The relative boiling points of the two isomeric glycol ethers are sufficiently different to enable recovery of a relatively pure form of n-butenyl glycol ether for further processing.

Instead of converting the separated sec-butenyl isomer into the n-butenyl isomer in a single step, the separated sec-butenyl glycol ether can also be fully back-cracked to ethylene glycol and butadiene. These starting materials can then be recycled into the addition reactor. Alternatively, the ethylene glycol and/or butadiene may be isolated for sale or other use.

In a further alternative embodiment, the separated sec-butenyl glycol ether is hydrogenated to form sec-butyl glycol ether.

According to a second aspect of the present invention, there is provided a process for the production of a saturated butyl glycol ether which comprises:

a. reacting butadiene with a saturated butyl glycol ether in the presence of a catalyst in a first reaction zone to produce a mixture of n-butenyl glycol ether and sec-butenyl glycol ether;

b. separating the n-butenyl glycol ether and secondary butenyl glycol ether formed in step a), c. hydrogenating the n-butenyl glycol ether separated in step b), and d. contacting the secondary butenyl glycol separated in step b) with a catalyst in a second reaction zone to convert the secondary butenyl glycol ether into the starting butadiene and saturated aliphatic glycol.

Preferably, the butadiene and saturated aliphatic glycol produced in step d is recycled to step a.

The addition step (a) of the second aspect of the present invention may be carried out using a heterogeneous or homogeneous catalyst. Where a heterogeneous catalyst is employed, the catalysts described above in connection with the first aspect of the present invention may be used. Such a heterogeneous catalyst may be employed in an unmodified state. Preferably, however, the heterogeneous catalyst is modified by the addition of at least one of the counterions described in relation with the first aspect of the present invention.

Where a homogeneous catalyst is employed for the addition step a), a soluble Bronsted or Lewis acids for example, sulphonic acid, triflic acid, and triflate salts may be used. Examples of such salts include lanthanide triflates, such as lanthanum and/or ytterbium trifluoromethanesulphonic acid salts.

Step d) of the second aspect of the present invention may be carried out in the presence of an acidic catalyst. Preferably, the catalyst employed in step d) is the same as the catalyst employed in step a). More preferably, the catalyst employed in both steps a) and d) are modified heterogeneous catalysts, such as those described in relation to the first aspect of the present invention.

Step d) is suitably conducted so that the reaction products are in the vapour phase and may be carried out at a temperature 80–250° C., preferably, 120 to 200° C. This stage can be conducted at elevated, atmospheric or sub-atmospheric pressures.

In a preferred embodiment, the reactions, a) and d) are carried out in separate reaction zones, for example, in different reactors under different conditions In both aspects of the present invention, the expression "butyl glycol ether" as used herein and throughout the specification is meant to indicate a compound of the chemical formula:

wherein R is an n-butyl group, each of $R^1$ and $R^2$ is hydrogen, or a hydrocarbyl group (for example, a $C_{1-10}$ alkyl, preferably, a $C_1$ to $C_4$ alkyl), and n=1 or more.

It should be understood that $R^1$ and $R^2$ may be the same or different.

In a preferred embodiment, $R^1$ and $R^2$ are H, such that the butyl glycol ether has the formula:

where R represents an n-butyl group and m is an integer having a value of 1 to 10. Preferably, m is an integer with a value of 1 to 3. Where m=1, the formula represents a n-butyl glycol ether of ethylene glycol which is abbreviated hereafter as "BGE". Where m=2, the formula represents a -n-butyl diglycol ether of diethylene glycol which is abbreviated hereafter as "BDGF".

Butadiene, which is a relatively inexpensive by-product of the refining process, is a potential feedstock for making butyl glycol ethers. Butadiene is commercially available either as a purified chemical or as a constituent of a hydrocarbon stream. In both aspects of the present invention, butadiene may be reacted with the saturated aliphatic glycol (step a or i) in either of these forms. An example of a suitable hydrocarbon stream having butadiene as a constituent is a mixed C4 stream commonly obtained from a naptha stream cracking process. Such a stream contains species such as butane, butene, 2-butene, isobutane, and isobutene. When such a mixed hydrocarbon stream is employed as a source of butadiene, other addition products such as a t-butyl ether may be produced when the hydrocarbon stream is contacted with the saturated aliphatic glycol. t-Butyl glycol ether may be cracked into isobutene and glycol. The latter may be recycled, whilst the former may be isolated for use, or further processing.

In the present process, the glycol reactant is suitably a saturated, aliphatic, straight chain glycol which has at least 2 carbon atoms, preferably 2–10carbon atoms and is most preferably ethylene glycol and diethylene glycol. Thus, the present process can be readily adapted to the reaction of butadiene with ethylene glycol to form a mixture of n-butenyl glycol ether and secondary butenyl glycol ether, the latter being separated and recycled to the initial stage and the n-butenyl glycol ether being catalytically hydrogenated to the desired n-butyl ether of ethylene glycol.

The addition reaction to form n-butenyl glycol ether is suitably carried out in a liquid or a mixed gas liquid phase. A reaction solvent maybe present. It is not essential that both the reactants dissolve completely in the solvent. However, it is an advantage if the solvent chosen is such that it is suitably capable of dissolving both the reactants. Specific examples of such solvents include hydrocarbons such as decane and toluene and non-protic oxygenated solvents such as esters and ethers e.g. butyl acetate, 1,2,-dibutoxyethane, tetrahydrofuran and 1,4-dioxane. The reaction products can also serve as solvents. For example, the butyl glycol ethers and the recycled sec-butenyl ether can also be used as a reaction solvents. In the mixed C4 stream case the t-butyl ethers can also be used as reaction solvents.

The presence of water as a reaction adjuvant can also beneficially affect the activity and selectivity of the catalysts. In the process of the present invention it is also advantageous to use polymerisation inhibitors such as eg alkylated phenols such as 2,6-di-tert-butyl-p-cresol (also known as "BHT" or butylated hydroxytoluene), other members of this series including the Irganox® series of materials (ex Ciba Gigy), the Lowinox® series of materials (ex Great Lakes Chemical Corporation); the Tropanol® series (ex ICI) and t-butylcatechol; nitroxides such as di-tert-butylnitroxide; N,N-dimethyl4-nitrosoaniline; nitric oxide and stable radicals such as 2,2,6,6-tetramethyl-piperidine-1-oxyl, 2,2,6,6-tetramethyl4-hydroxypiperidine-1-oxyl and 2,2,6,6-tetramethylpyrrolidine-1-oxyl to prevent the polymerisation and/or oligomerisation of the butadiene reactant into unwanted polymers in the presence of the aforementioned acidic catalysts.

It has been found that the selectivity and activity of step i) is dependent on the level of water in the reaction mixture. At levels above 5% w/w the catalyst activity is significantly reduced compared to the activity observed at about, 0.1 to 0.7w/w %. This reduced activity can be offset by raising the reaction temperature but this can lead to reduced reaction selectivity. Consequently the water level in the reaction mixture of step i/a is suitably in the range from 0 to 5%w/w on the glycol reactant, preferably from 0.05 to 1% w/w.

The relative mole ratios of butadiene to the glycol reactant in the addition reaction is suitably in the range from 5:1 to 1:50, preferably in the range from 1:1 to 1:10. It is believed that the presence of a marginal excess of glycol reactant may improve the reaction selectivity and prevent the formation of oligomers and disubstitution of the ethylene glycol. However, very large excesses may lead to unnecessary costs being incurred due to the need to recycle.

The butadiene reactant may be added to the addition reaction in a stepwise fashion, i.e. not all at once, in two or more stages to a batch reactor. Alternatively, the butadiene reactant may be added at a series of points along the length of a flow reactor. This may be advantageous because the reaction between butadiene with itself is likely to be second order whereas the reaction between alcohol and butadiene is likely to be first order and hence keeping the standing concentration of butadiene low is likely to improve the reaction selectivity.

This addition reaction is suitably carried out at a temperature in the range of from of 20 to 170° C., preferably, 20 to 150° C., more preferably, between 50 and 150° C., and most preferably, between 70 and 120° C. The reaction is suitably carried out at the autogenous reaction pressure which is determined by factors such as the reaction temperature, presence or absence of solvent, excess of reactants and impurities present in the butadiene stream. An additional pressure may be applied to the system if single fluid phase is preferred e.g. no butadiene gas phase in addition to the solvated liquid phase.

The addition reaction may be suitably carried out in a plug flow reactor, with the unused butadiene being flashed off and recycled to the reactor via a vapour liquid separator, but equally could be conducted in a slurry reactor. In the case of a plug flow reactor, the butadiene can be present partially as a separate gas phase as well as being dissolved and this would result in either a trickle bed operation or a bubble bed operation. A typical LHSV (liquid hourly space velocity= volume of liquid feed per h/catalyst bed volume) for the glycol is 0.2 to 20(e.g. 0.5 to 20), more preferably 1 to 5. In the case of a slurry reactor, a continuous bleed of any deactivated catalyst can be taken. It is economically advantageous to run with catalyst in a various stages of deactivation to improve the utilisation of catalyst. In this case the total loading of catalyst (activated+deactivated) can reach high levels such as 50% w/w of the reaction charge.

In the process, distillation columns are used to provide the separation of the isomeric butenyl glycol ethers, i.e. the n-butenyl glycol ether and secondary butenyl glycol ether. Water will give rise to azeotroping mixtures which can hinder the separation of the glycol ethers. This problem can be alleviated by using low levels of water. The sec-butenyl glycol ether can be optionally recovered and recycled to the initial addition reaction between butadiene and the glycol in order to improve the economics of the process. It has been found that the sec-butenyl glycol ether under reaction conditions interconverts with n-butenyl ether. The conversion of the sec-butenyl glycol ether to glycol and butadiene can be achieved by treatment in the vapour phase with a acidic support such as an alumina. The use of such a separate pre-treatment prior to the return to the addition reactor may be beneficial on reaction rate and selectivity grounds.

Where the secondary butenyl glycol ether is isomerised to the corresponding n-butenyl glycol ether, this isomerisation is suitably carried out in the presence of the glycol as a solvent. The solvent can also be an aliphatic or aromatic hydrocarbon solvent which may be substituted by halogen atoms. Suitable solvents include 1) dichlorobenzene; 2) the polyoxyalkylene glycol ethers such as diethylene glycol di methyl ether, triethylene glycol dimethyl ether, triethylene glycol dibutyl ether; 3) sulphoxides such as dimethyl sulphoxide; 4) dimethyl sulphone; and 5) sulpholane.

The relative boiling points of the two isomeric glycol ethers are sufficiently different to enable recovery of a relatively pure form of n-butenyl glycol ether for further processing.

To convert n-butenyl glycol ethers to n-butyl glycol ethers the former has to be subjected to a hydrogenation step. It is preferable to carry out the hydrogenation step under heterogeneous conditions so that it is easy to separate the catalyst from the reaction products. The catalytic hydrogenation step is suitably carried out using one or more of the following catalysts: transition metal catalysts, typically from the later groups such as ruthenium, platinum, nickel, palladium, preferably supported on a low acidity carrier such as carbon or coating a support so that little free acidity remains. Residual acid sites may result in a reduction in selectivity. Examples include Raney nickel or supported Raney nickels, or 5% ruthenium on carbon. The preferred hydrogenation catalysts are a Raney nickel catalyst supported on carbon and a ruthenium catalyst supported on carbon.

This hydrogenation is suitably carried out at a temperature in the range from 20 to 200° C., preferably from 40 to 160° C. The hydrogenation reaction is suitably carried at a pressure in the range from 1 barg to 100 barg, preferably from 5 to 50 barg. The hydrogenation can be carried out in slurry and flow reactors. A solvent is not necessarily required for this reaction. The reaction can be carried out in an all gas or vapour phases or as a two phase mixture with mixed gas and liquid. In the latter case a flow reactor would be operated in either a trickle bed or a bubble bed mode. The completion of the hydrogenation of the n-butenyl glycol ethers can be determined conveniently for batch reactions by cessation of hydrogen uptake and in the case of both flow and batch reactors by sampling and analysis by methods such as Gas Chromatography and UV.

The process of the present invention has the following advantages:

i. The amount of by-products is much less than in conventional routes such as e.g. reaction of butanol with an olefin oxide;

ii. The butadiene based routes can be adapted to produce a variety of n-butyl glycol ethers, including inter alia butyl diglycol ether and butyl propylene glycol ether by varying the glycol reactant.

iii. The proposed C4 butadiene based routes use relatively mild reaction conditions and relatively inexpensive catalysts.

BRIEF DESCRIPTION OF THE DRAWINGS

The invention will be further described with reference to the accompanying drawings, in which.

EXAMPLES

Example 1

Addition of Butadiene to Ethylene Glycol

Figure 1:
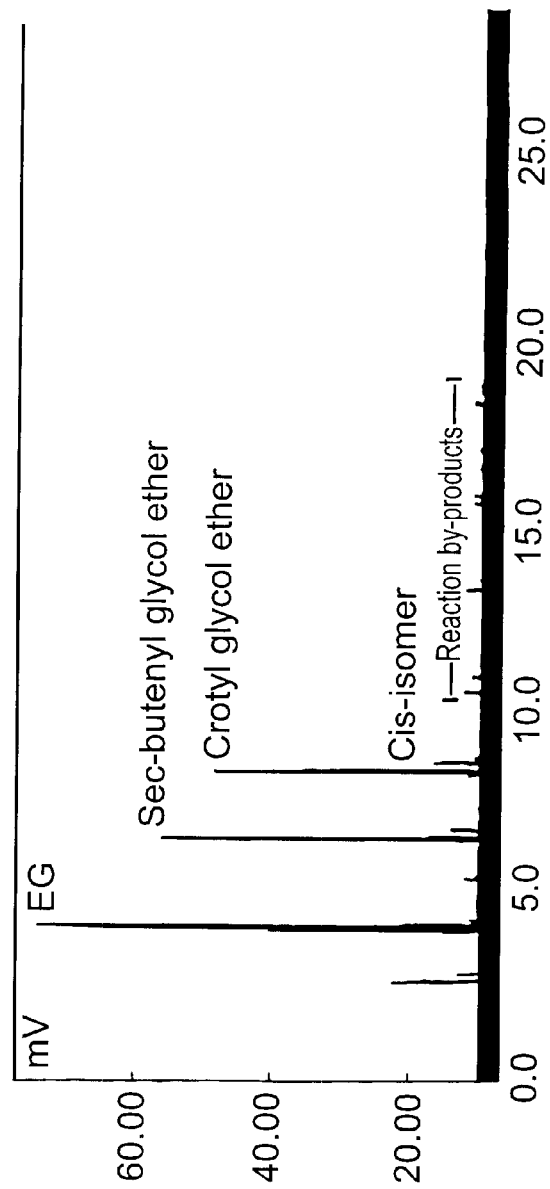
FIG. 1 is a gas chromatography trace of the reaction described in Example 1.
Figure 2:
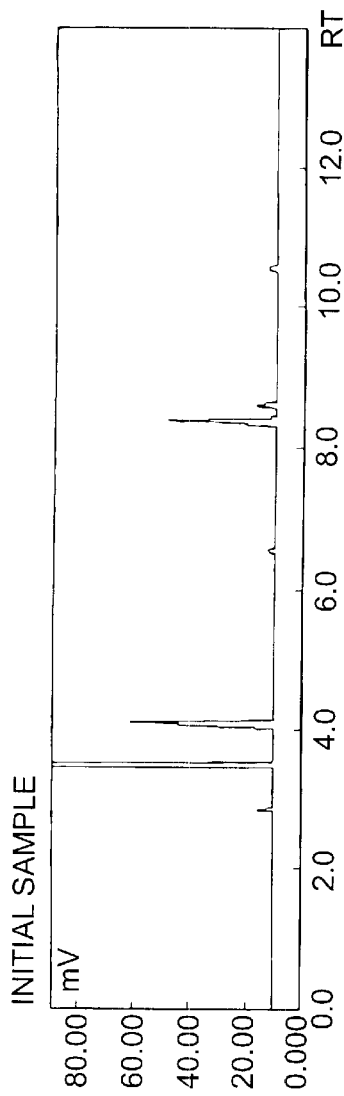
FIGS. 2 and 3 are gas chromatography traces of the reaction described in Example 2.
Figure 3:
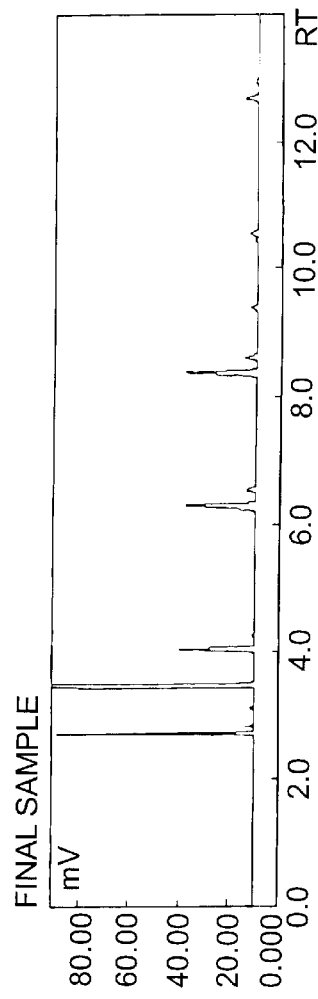

To a 10 litre stainless steel autoclave was charged 85 g of washed Amberlyst® 15H ion-exchange resin to a stainless steel "tea bag" mounted around the impeller shaft. To this was charged, for run BS1 ethylene glycol (3600 g, ex Aldrich) and after nitrogen purging of the system and heating to 90° C., butadiene (750 g). In the case of run BS2, the above charge was repeated, except that water (78 g) was added with the ethylene glycol. The progress of the reaction was monitored by GC and a typical GC trace of this reaction is shown in FIG. 1.

As can be seen, the reaction predominantly gives similar quantities of the sec-butenyl and crotyl glycol ethers. The small peak on the side of the sec-butenyl glycol has is been identified as the di-butenyl glycol ether (by GC/MS fragmentation patterns) of ethylene glycol, that is the product obtained from adding a molecule of butadiene to both hydroxyl groups of ethylene glycol. The table below gives product distribution for the two reactions, the GC response factor for n-butyl glycol ether was used for all the glycol containing materials.

| Run No. | Runtime (minutes) | sec-butenyl glycol ether (% w/w) | crotyl glycol ether (% w/w) | 4-vinyl cyclohexene (% w/w) | oligomers (% w/w) |
|---|---|---|---|---|---|
| BS1 | 1440 | 10.6 | 11 | 0.4 | 4.1 |
| BS2 | 1440 | 6.2 | 6.5 | 0.06 | 1.2 |

From the above it can be seen that the addition of water improves the reaction selectivity (reducing higher oligomers relative to C4 products) whilst reducing the reaction rate. The reaction selectivities to the two C4 glycol ethers are BS1=73% and BS2=83.2%.+.

Example 2

Isomerisation of C4 glycol ether isomers

A sample of the final product of the autoclave direct addition reaction of butadiene to ethylene glycol, BS 1 prepared as described previously, was rotary evaporated at 9 mbar, 80° C., this served to concentrate the lower boiling butenyl glycol ethers. This distillate sample was then farther distilled with a packed column (4 mbar, 55 ° C.) to concentrate in the distillate the sec-butenyl glycol ether isomer and in the kettle the crotyl glycol ether isomer.

A mixture of concentrated sample (100 g), ethyl acetate (184 g) and decane (1.2637 g-internal reference) was heated to 50° C. in the presence of Amberlyst® 15resin (15 g) for 5 h. Samples of the initial and final product were analysed by gas chromatography.

See attached spectrum for the results of a run with a sample rich in crotyl glycol ether. The top trace represents the starting mixture rich in crotyl glycol ether (retention time ~8.35 min).The bottom trace shows the final reaction product in which the sec-butenyl glycol ether (6.3 min) has grown. Identical results were observed for experiments with samples rich in the sec-butenyl glycol ether isomer. In both cases an approximate 1:1 ratio of isomers was obtained as a final product.

The main peaks that are observed are:

| | |
|---|---|
| Ethyl acetate | 3.5 min |
| Ethylene glycol | 4.1 min |
| Sec-butenyl glycol ether | 6.3 (and 6.5) min |
| n-butenyl glycol ether | 8.35 (and 8.6) min |
| Decane | 10.5 min |

Example 3

Hydrogenation of Crotyl Glycol Ether

The hydrogenation was carried out in a batch, stirred autoclave (500 ml zirconium metal) which was initially charged with:

| | |
|---|---|
| Concentrated crotyl glycol ether fraction | 60 g |
| Toluene | 240 g |
| Decane | 2.99 g |
| Catalyst (Ni/C Harshaw supported Raney, ground .60 mesh) | 6. g |

The autoclave was charged, purged with nitrogen, pressure tested and then pressurised to 30 bar with hydrogen. The reaction mixture was heated to 100° C. with stirring at 1000 rpm for 16 hrs. A gas ballast vessel was used to maintain the autoclave pressure at 30 bar. The final reaction mixture was analysed by GC which confirmed that 100% conversion of the crotyl glycol ether to give a high yield (estimated at >95%) of n-butyl glycol ether.

Example 4

These experiments were conducted in a 10 litre stainless steel batch autoclave. The autoclave was charged with an Amberlyst 15H® catalyst (85 g, see below), ethylene glycol (3500 g) and polymerisation inhibitor (1000 ppm 4-t-butyl catechol), and the reaction mixture was heated to 90° C. At the same time, a feed vessel was filled with 700 g of 1,3-butadiene. The autoclave was allowed to reach the required temperature, and the 1,3-butadiene was added to the autoclave as one aliquot. The course of reaction was monitored by taking regular samples. The samples were analysed by GC. The reaction was repeated three times using the same catalyst at 90° C., 100° C. and 110° C . The Amberlyst 15H® catalyst had 4.5% of its sites exchanged with a tetraphenyl phosphonium counterion.

The reaction conditions employed are summarised in the table below.

| Temperature (° C.) | 90 | 100 | 110 |
|---|---|---|---|
| Ethylene glycol (g) | 3612 | 3624 | 3586 |
| butadiene (g) | 270 | 224 | 204 |
| inhibitor 4-TBC | 1.8 | 1.8 | 1.8 |
| DEGDEE (g) | 35.8 | 38.2 | 36.4 |

The following definitions were used:
Conversion=reactant consumed/reactant introduced
Selectivity=desired product/reactant consumed
The results are as follows:
For the 90° C. run after (after a run time of 4 h and 23 min).
Conversion of ethylene glycol: 20%
Selectivity on C4's formation: 98%
For the 100° C. run after (after a run time of 2 h and 59 mn).
Conversion of ethylene glycol: 22%
Selectivity on C4's formation: 98%
For the 110° C. run after (after a run time of 3 h and 45 min).
Conversion of ethylene glycol: 29%
Selectivity on C4's formation: 96.5%

What is claimed is:

1. A process for the production of n-butyl glycol ether which comprises:
    i. forming a mixture of n-butenyl glycol ether and secondary butenyl glycol ether by reacting butadiene with a saturated aliphatic glycol in the presence of a heterogeneous catalyst which is modified by the addition of at least one counterion selected from the group consisting of: an alkyl pyridinium, quaternary ammonium, quaternary arsonium and quaternary phosphonium;
    ii. separating the n-butenyl glycol ether and secondary butenyl glycol ether formed in step i), and
    iii. hydrogenating the n-butenyl glycol ether separated in step ii) in the presence of a catalyst to the corresponding n-butyl glycol ether.

2. A process as claimed in claim 1, wherein the secondary butenyl glycol ether separated from the mixture of crotyl glycol ether and secondary butenyl glycol ether is recycled back to step i).

3. A process for the production of a saturated butyl glycol ether which comprises:
    a. reacting butadiene with a saturated glycol ether in the presence of a catalyst in a first reaction zone to produce a mixture of n-butenyl glycol ether and sec-butenyl glycol ether;
    b. separating the n-butenyl glycol ether and secondary butenyl glycol ether formed in step a),
    c. hydrogenating the n-butenyl glycol ether separated in step b), and
    d. contacting the secondary butenyl glycol ether separated in step b) with a catalyst in a second reaction zone to convert the secondary butenyl glycol ether into the starting butadiene and saturated aliphatic glycol.

4. A process as claimed in claim 3, wherein the n-butenyl glycol ether separated in step b) is hydrogenated in step c) in the presence of a heterogeneous catalyst.

5. A process as claimed in claim 3, wherein step a) is carried out in the presence of a catalyst which is modified by the addition of a counterion selected from the group consisting of: an alkyl pyridinium quaternary ammonium, quaternary arsonium and quaternary phosphonium.

6. A process as claimed in any preceding claim wherein the n-butyl glycol ether produced is a mono-n-butyl ether of ethylene glycol.

7. A process as claimed in claim 1 wherein the butadiene employed in step i) is in the form of a feed stream consisting essentially of butadiene, or is in the form of a hydrocarbon stream comprising butadiene.

8. A process as claimed in claim 1, wherein the catalyst employed to catalyse the reaction between butadiene and the saturated aliphatic glycol is a heterogeneous catalyst selected from the group consisting of: liquid acidic polymers, HY zeolites, strong acid macrorecticular and gel type ion exchange resins and supported heteropolyacids of tungsten or molybdenum.

9. A process as claimed in claim 3, wherein the catalyst in the second reaction zone is a Brønstead or Lewis acid.

10. A process as claimed in claim 9, wherein the catalyst in the second reaction zone, is the same as the catalyst employed in the first reaction zone.

* * * * *